US012774444B2

(12) United States Patent
Huang et al.

(10) Patent No.: US 12,774,444 B2
(45) Date of Patent: Oct. 27, 2026

(54) HIGH-THROUGHPUT ELECTROPORATION ASSEMBLY

(71) Applicant: Massachusetts Institute of Technology, Cambridge, MA (US)

(72) Inventors: Po-Hsun Huang, Quincy, MA (US); Cullen Richard Buie, Cambridge, MA (US); Sijie Chen, Cambridge, MA (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 1384 days.

(21) Appl. No.: 17/390,435

(22) Filed: Jul. 30, 2021

(65) Prior Publication Data

US 2022/0098540 A1 Mar. 31, 2022

Related U.S. Application Data

(60) Provisional application No. 63/085,707, filed on Sep. 30, 2020.

(51) Int. Cl.
*C12M 1/42* (2006.01)

(52) U.S. Cl.
CPC .................................. *C12M 35/02* (2013.01)

(58) Field of Classification Search
CPC ..................................................... C12M 35/02
See application file for complete search history.

(56) References Cited

U.S. PATENT DOCUMENTS

| | | | | |
|---|---|---|---|---|
| 5,539,362 | A * | 7/1996 | Culling | H01P 5/185 333/116 |
| 7,678,564 | B2 | 3/2010 | Müller-Hartmann et al. | |
| 9,039,883 | B2 | 5/2015 | Guerrieri et al. | |
| 10,376,889 | B1 | 8/2019 | Masquelier et al. | |
| 10,415,058 | B2 | 9/2019 | Bernate et al. | |

(Continued)

FOREIGN PATENT DOCUMENTS

| | | | | |
|---|---|---|---|---|
| GB | 2523579 | A | 9/2015 | |
| WO | WO-0107585 | A1 * | 2/2001 | A61B 5/0536 |

(Continued)

OTHER PUBLICATIONS

BTX Harvard Apparatus: Molecular Delivery Systems, "HT 96 and 25 Well Electroporation Plates," www.btxonline.com, date unavailable, 2 pages.

(Continued)

*Primary Examiner* — Michael A Marcheschi
*Assistant Examiner* — Jonathan E Lepage
(74) *Attorney, Agent, or Firm* — Hamilton, Brook, Smith & Reynolds, P.C.

(57) ABSTRACT

An electroporation assembly for interfacing with a liquid handling system includes at least two electrically conductive layer components and a channel layer component. The channel layer component is configured to be removably disposed between the electrically conductive layer components. The electrically conductive layer components and the channel layer component define a plurality of parallel electroporation flow paths in an assembled state. An electroporation system includes an electroporation assembly and a cell collection unit. The electroporation assembly is configured to direct a flow of a cell sample to the cell collection unit.

19 Claims, 8 Drawing Sheets

(56) References Cited

U.S. PATENT DOCUMENTS

| | | | |
|---|---|---|---|
| 10,450,543 | B2 | 10/2019 | Chang et al. |
| 10,947,526 | B2 | 3/2021 | Buie et al. |
| 2006/0115888 | A1 | 6/2006 | Gamelin et al. |
| 2017/0211128 | A1 | 7/2017 | Talebpour et al. |
| 2018/0179485 | A1 | 6/2018 | Borenstein et al. |
| 2018/0362908 | A1 | 12/2018 | Borenstein et al. |
| 2019/0136224 | A1 | 5/2019 | Garcia Dominguez et al. |
| 2020/0332276 | A1 | 10/2020 | Buie et al. |

FOREIGN PATENT DOCUMENTS

| | | | | |
|---|---|---|---|---|
| WO | 2017210334 | A1 | 12/2017 | |
| WO | WO-2019059936 | A1 * | 3/2019 | .............. C12M 1/42 |

OTHER PUBLICATIONS

"Notification of Transmittal of the International Search Report and the Written Opinion of the International Searching Authority, or the Declaration," issued for International Application No. PCT/US2021/043934, entitled "High-Throughput Electroporation Assembly," mailed on Nov. 19, 2021.

* cited by examiner

HIGH-THROUGHPUT ELECTROPORATION ASSEMBLY

RELATED APPLICATION

This application claims the benefit of U.S. Provisional Application No. 63/085,707, filed on Sep. 30, 2020. The entire teachings of the above application are incorporated herein by reference.

GOVERNMENT SUPPORT

This invention was made with Government support under Grant No. R01 DE027850 awarded by the National Institutes of Health (NIH). The government has certain rights in the invention.

BACKGROUND

One of the key steps in bacterial genetic engineering processes is the delivery of genetic materials into bacterial cells, which can be realized mainly by viral (e.g., bacteriophage) mechanical, chemical, and electrical methods. Among these different methods, electroporation has been a preferred method because electroporation can provide for delivery of both small and large molecules, is not cell-type specific, and provides for relatively high efficiency.

Electroporation is typically performed by cuvette-based, batch-wise methods that rely on manual pipetting. When analyzing a new or unknown bacterial species/strain, for example, electroporation conditions that lead to successful genetic transformation need to be identified. Such identification can be very difficult as the parametric space that can potentially lead to successful reversible transformation is very large.

To improve throughput over cuvette-based approaches, some companies have generated multi-well systems. For example, the 96-well Shuttle™ system made by Lonza, for example, offers medium-throughput transformation but is applicable only for mammalian cells and still requires extensive manual pipetting. Another example is the 96-well electroporation plate made by BTX; however, BTX's plates suffer from a high rate of arcing events and malfunction upon encountering an arcing issue.

SUMMARY

An electroporation assembly is provided that can be used with various liquid handling and liquid collection systems for high-throughput electroporation. Such electroporation assemblies can provide for a scalable, high throughput electroporation platform that is compatible with commercially available liquid handling robots for automated pipetting.

The electroporation assembly can include layer components that are configured to be assembled in a layer-wise assembly and disassembled from one another such that at least some layer components may be reusable or replaceable by matching layer components. The layer components can include or otherwise engage with self-sealing structures to provide for electroporation flow paths that are fluidically sealed from one another when the layer components are in an assembled state.

An electroporation assembly includes at least two electrically conductive layer components and a channel layer component configured to be removably disposed between the electrically conductive layer components. When in an assembled state, the electrically conductive layer components and the channel layer component define a plurality of parallel electroporation flow paths.

The electroporation assembly can also include one or more support layer components, which can interface with the electrically conductive layer components and which can comprise an electrically insulating material. Any of the layer components of the electroporation assembly can be removeable, reusable, disposable, interchangeable, autoclavable, or a combination thereof.

The support layer components can be configured to seal against the electrically conductive layer components. For example, the support layer components can include a sealing structure configured to engage with a complimentary sealing structure of the electrically conductive layer components, a sealing layer component can be disposed between the support layer and conductive layer components, or a combination thereof. The support layer components can also define a plurality of input or output ports. The input ports can be configured to receive cell sample fluid from a manual pipette, an automated liquid dispenser, or an automated liquid handling system. The output ports can each include a nozzle or be configured to receive a nozzle of a conductive layer component to direct a fluid flow exiting the assembly. The inlet and outlet ports can each be configured to connect with, respectively, a sample reservoir or a collection unit such that cell sample fluid entering and/or exiting the assembly is sealed (e.g., not exposed to air or to an ambient environment).

The conductive layer components can be configured to produce an electric field within each of the electroporation flow paths or within a subset of the electroporation flow paths. For example, the conductive layer components can each be uniformly conductive or can include selectively activatable regions or electrodes capable of producing electric fields that vary in at least one of strength and timing for a subset of the electroporation flow paths. One of the at least two conductive layer components can comprise nozzles at terminating ends of the electroporation flow paths. The nozzles can be configured to direct a flow of a cell sample fluid travelling through each of the electroporation flow paths into corresponding receptacles of a cell collection unit.

The channel layer component can include an electrically insulating material and can define a constriction region for each of the electroporation flow paths of the assembly. The channel layer component can include a sealing structure configured to engage with a complimentary sealing structure of another layer component. Sealing structures of the support, conductive, and/or channel layer components can be configured to be self-sealing. The constriction regions defined by the channel layer can be of a same or differing geometry. For example, a subset of the constriction regions of a single channel layer can vary in geometry with respect to other constriction regions defined by that channel layer. A geometry of the constriction regions can be of a uniform cross-sectional area or a varying cross-sectional area, for example, providing for a converging channel, a diverging channel, or a converging and diverging channel. One or more channel layers can be included in an assembly. Where two or more channel layers are included in an assembly, each can define a portion of the plurality of the electroporation flow paths, thereby providing for configurable constriction regions.

An electroporation system can include an electroporation assembly and a cell collection unit, such as a reservoir, a multi-reservoir device, or a multi-well plate. The electroporation assembly can be configured to direct a flow of a cell sample to the cell collection unit for high-throughput processing. The system can further include a liquid handling system, such that the electroporation assembly is configured to receive a flow of a cell sample from the liquid handling system. A power source can be included in the system and in operative arrangement with the electrically conductive layer components to deliver a voltage differential thereto. For example, electrical pulses can be delivered by the conductive layer components to effect electroporation of a cell sample flowing through the electroporation assembly.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Figure 1:
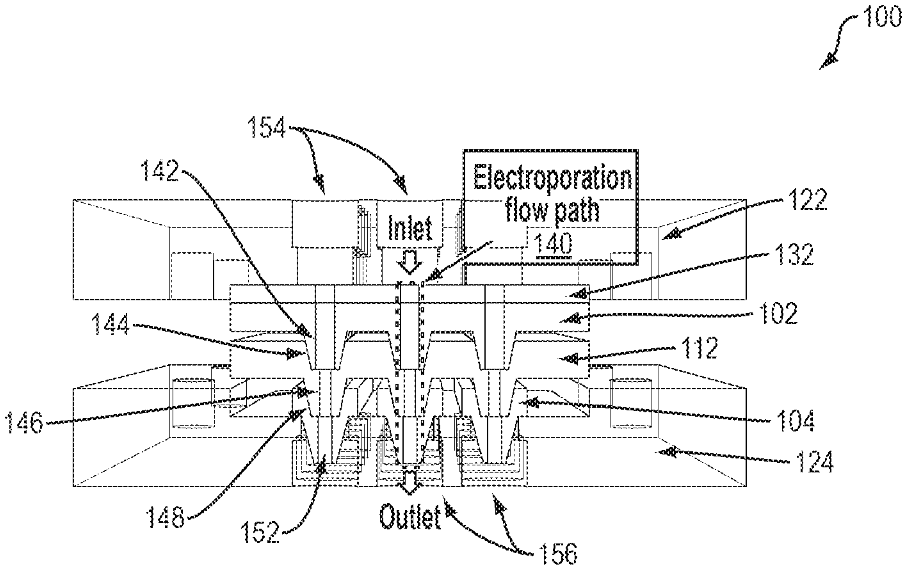
FIG. 1 is a schematic of an electroporation assembly comprising layer components.

FIG. 1 illustrates an example of an electroporation assembly 100 comprising layer components, including at least two conductive layer components 102, 104 (e.g., top 102 and bottom 104 electrode layers) and at least one channel layer component 112. The channel layer component 112 is removably disposed between the at least two conductive layer components 102, 104. When assembled, the at least two conductive layer components 102, 104 and the channel layer 112 component define a plurality of parallel electroporation flow paths 140 (one of which is represented by dash overlay in FIG. 1).

Figure 2:
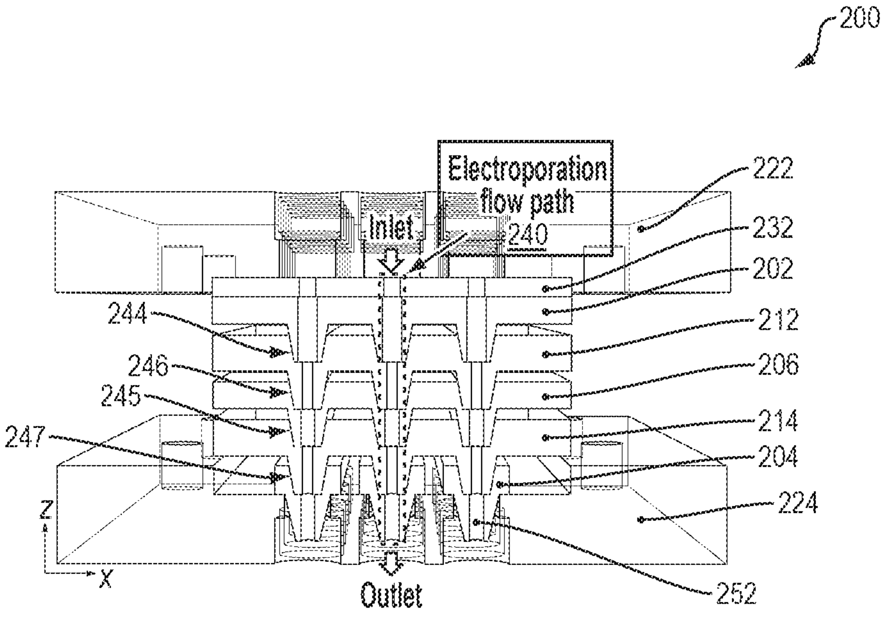
FIG. 2 is a schematic of an electroporation assembly in which multiple channel layer components and multiple electrode layer components are included.

FIG. 2 illustrates another example of an electroporation assembly 200 in which more than two conductive layer components and more than one channel layer component are included. As illustrated, first and second channel layer components 212, 214 are disposed between electrode layers 202, 204. A middle electrode layer 206 is included between the first and second channel layer components. As illustrated, the electrode and channel layer components can be arranged to provide for configurable electroporation flow paths 240 within the assembly. A number of conductive layer components and channel layer components within a device can be varied, and, for example, middle electrode layers (e.g., middle electrode layer 206) can be optional.

An electroporation assembly can further include one or more support layer components, which can be electrically insulating. As illustrated in FIGS. 1 and 2, a top support layer 122, 222 can be configured to interface with the top conductive layer component 102, 202, and a bottom support layer 124, 224 can be configured to engage with the bottom conductive layer component 104, 204. The one or more support layer components can include or engage with a sealing layer component (e.g., sealing layer 132, 232), include sealing structures (e.g., such as sealing structures 142, 144, 146, 148 illustrated with respect to other layers), or both. Complementary sealing structures can be included in any of the support layer components, conductive layer components, and channel layer component(s). For example, as illustrated in FIG. 1, the sealing structures 142 of the conductive layer component 102 can engage with complementary sealing structures 144 of the channel layer component 112. As illustrated, the sealing structures 142 are protrusions and the complementary sealing structures 144 are recesses; however, alternative configurations are possible. For example, the sealing structures of an assembly can be protrusions that are oriented to extend upwards instead of downwards with respect to the orientation of the assembly 100 as shown in FIG. 1 and may be of a different shape. As further illustrated in FIG. 1, the channel layer component 112 includes sealing structures 146 that engage with complementary sealing structures 148 of the bottom conductive layer component 104.

Such sealing structures and complementary sealing structures can be integral with or embedded within the respective layer components to provide for a self-sealing or self-bonding assembly. The sealing structures can prevent leakage or cross-contamination between or among the plurality of electroporation flow paths. Alternatively, or in addition to sealing structures, bonding material, such as an electrically-insulating tape, can be disposed between layers of an assembly, as shown in the example of FIG. 6B.

Figure 4:
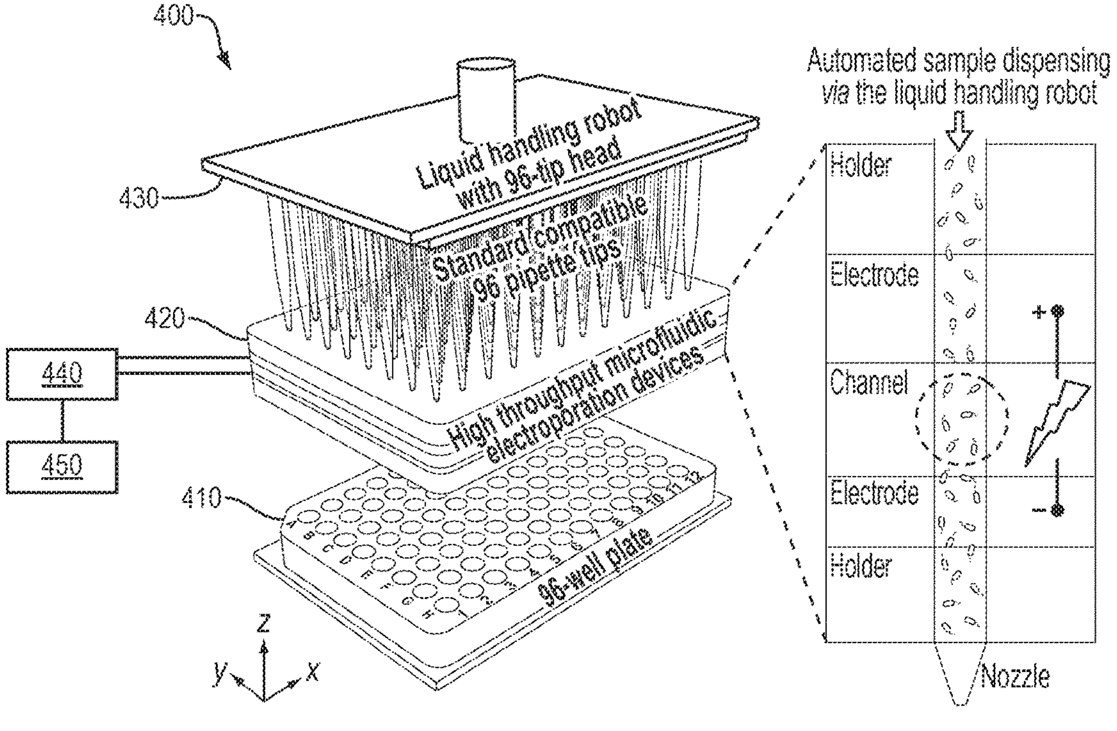
FIG. 4 is a schematic of an electroporation system.

As further illustrated in FIGS. 1 and 2, nozzles 152, 252 can be included to direct a flow or fluid from the apparatus to a collection unit. The nozzles can be included in a conductive layer component (as shown in FIG. 1) or in a support layer component (as schematically illustrated in FIG. 4). The nozzles can be integral with or embedded within the respective layer component to provide for a directed fluid flow and prevent pooling at an outlet end of the assembly.

At least one support layer component can be an inlet support layer component that defines a plurality of inlet ports. For example, as illustrated in FIG. 1, the top support layer 122 defines inlet ports 154. The inlet ports can be configured to receive cell sample fluid from a manual pipette, an automated liquid dispenser, and/or an automated liquid handling system. Alternatively or in addition, the inlet ports can be configured to connect with one or more cell sample reservoirs or tubes such that cell sample fluid entering the assembly from the one or more cell sample reservoirs is not exposed to air (e.g., a flow path from the sample reservoir to the electroporation assembly is sealed). The cell sample fluid can then be directed through the electroporation flow paths 140.

At least one support layer component can be an outlet support layer component that defines a plurality of outlet ports. For example, as illustrated in FIG. 1, the bottom support layer 124 defines outlet ports 156. The outlet ports can optionally be configured to connect with one or more collection reservoirs such that cell sample fluid exiting the assembly to the one or more collection reservoirs is not exposed to air. As illustrated in FIG. 1, the outlet ports 156 are configured to receive nozzles 152 that are included in the conductive layer 104; however, the outlet ports can alternatively be configured to define nozzles. For example, the bottom support layer 124 can include sealing structures that are complementary to the conductive layer 104, and the support layer 124 can define a nozzle structure for outputting the fluid sample.

Sealing structures can be configured to provide for self-sealing or self-bonding of any number of conductive layers and channel layers to be provided in an assembly. As illustrated in FIG. 2, channel layers 212, 214 can include complementary sealing structures 244, 245 for engaging respective sealing structures of the conductive layers 202, 206. Likewise, conductive layers 204, 206 can include complementary sealing structures 246, 247 for engaging respective sealing structures of the channel layers 212, 214.

The conductive layer components, the channel layer components, and the support layer components can each be removeable, reusable, interchangeable, autoclavable, or any combination thereof.

The conductive layer components (e.g., 102, 104) of an assembly can be configured to produce an electric field within each of the plurality of electroporation flow paths. The electric field produced within the electroporation flow paths can be uniform throughout the assembly or can vary. For example, at least one of the conductive layer components of an assembly can be uniformly conductive. Alternatively, the conductive layer components of an assembly can be configured to produce an electric field within a subset of the plurality of electroporation flow paths included within the assembly. For example, at least one of the conductive layer components can include selectively activatable electrodes capable of producing electric fields that vary in at least one of strength and timing for a subset of the plurality of electroporation flow paths. An electric field within each electroporation flow path can also vary where the flow paths have different cross-sectional dimensions or geometries.

The channel layer component can define a constriction region for each of the electroporation flow paths defined by an assembly. The construction region can be of a geometry having a uniform cross-sectional area or a varying cross-sectional area (e.g., a converging channel, a diverging channel, or a converging and diverging channel). The constriction regions defined by a channel layer can be geometrically uniform throughout the layer, or can vary for at least a subset of the channels defined by the channel layer.

Figure 3A:
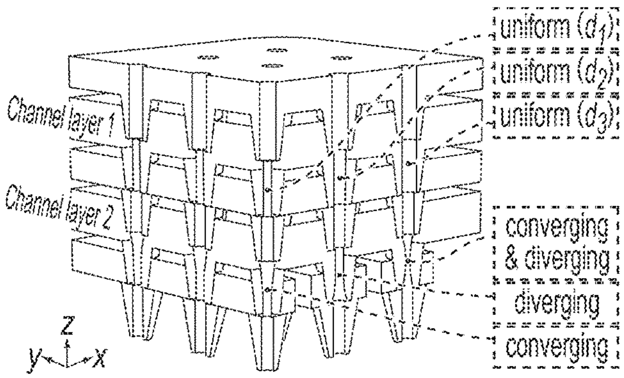
FIG. 3A is a schematic of an electroporation assembly comprising two channel layer components, one of the channel layer components providing for constriction regions of uniform cross-sectional geometries, the geometries each varying in diameter, and the other of the channel layer components providing for constriction regions of varying cross-sectional geometries, including converging, diverging, and converging and diverging.
Figure 3B:
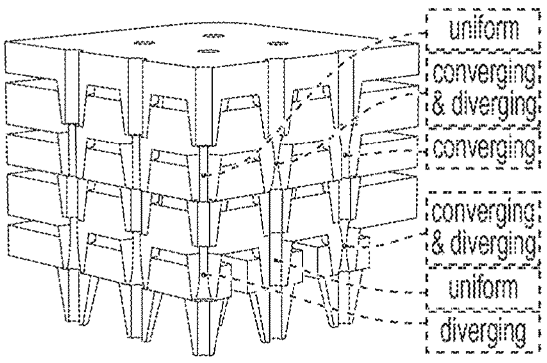
FIG. 3B is a schematic of an electroporation assembly comprising two channel layer components, each of the channel layer components providing for constriction regions of varying cross-sectional geometries.

FIGS. 3A and 3B illustrate example configurations of electroporation assemblies with channel layer components providing for varying constriction region geometries. A channel layer component can define constriction regions that are uniform throughout the layer (e.g., all constriction regions are of a same geometry and a same size, as shown in FIG. 2). Alternatively, a channel layer component can define constrictions regions of similar cross-sectional geometry but which vary in size (e.g., as shown in "Channel layer 1" of FIG. 3A), or can define constriction regions of differing cross-sectional geometries and/or differing sizes (e.g., as shown in the "Channel layer 2" of FIG. 3). The channel layer components can be arranged to provide for configurable electroporation flow paths in which differing (or similar) constriction regions are combined, as shown in FIG. 3B.

Constriction regions can be of a single diameter or of a varying diameter within range of about 0.1 mm to about 10 mm, or of about 0.5 mm to about 5 mm (e.g., 0.45 mm, 0.5 mm, 1 mm, 2 mm, 3 mm, 4 mm, 5 mm, 5.1 mm). A length of a construction region can be within range of about 1 mm to about 50 mm, or of about 5 mm to about 30 mm (e.g., 4.5 mm, 5 mm, 10 mm, 15 mm, 20 mm, 25 mm, 30 mm, 30.5 mm).

Examples of constriction regions of electroporation flow paths of varying geometries are further shown and described in WO2016/003485, the entire teachings of which are incorporated herein by reference.

While FIGS. 1-3B illustrate configurations in which channel layers and conductive layers alternate with one another, other layering configurations are possible. For example, two channel layer components can be arranged in serial to provide for an extended and/or varying constriction region between two conductive layers of an assembly.

An electroporation system 400 is shown in FIG. 4. The electroporation system includes a cell collection unit 410 and an electroporation assembly 420. The electroporation assembly is configured to direct a flow of a cell sample to the cell collection unit. As illustrated in FIG. 4, the cell collection unit is a 96-well plate; however, the cell collection unit can be a multi-well plate of a differing dimension, a reservoir, or a multi-reservoir device, for example.

The electroporation system can further include a liquid handling system 430. The electroporation assembly can be configured to receive a flow of a cell sample from the liquid handling system. As illustrated in FIG. 4, the liquid handling system is a multi-channel pipette system; however, the liquid handling system can be any other liquid dispensing device (e.g. a fluid reservoir with dispensing tubes).

The electroporation system can further include a power source 440 in operative arrangement with conductive layer components of the electroporation assembly 420 to deliver a voltage differential thereto. The power source 440 and, optionally, an associated controller 450, can be configured to deliver electrical pulses to the plurality of electroporation flow paths.

Examples of high-throughput electroporation systems that include components such as liquid handling systems and cell-collection units are further shown and described in WO 2017/2103345, the entire teachings of which are incorporated herein by reference.

Electroporation assemblies and systems as described herein can provide for high-throughput transformation and can overcome several shortcomings of standard cuvette-based, batch-wise methods as well as conventional medium- and high-throughput methods. In an example, when analyzing a new (or unknown) bacterial species/strain, one first needs to identify electroporation conditions that can lead to successful genetic transformation. Determining successful electroporation conditions can be very difficult with existing electroporation approaches because the parametric space that could lead to successful reversible transformation is very large. Given that the cuvette-based electroporation approach heavily relies on manual pipetting, identifying the conditions for successful transformation of a new or unknown bacterial species can become an overwhelming task with human error and biases. For example, if there are five electroporation parameters, each with six to eight different conditions to be tested, it would—at a rate of a few dozen electroporation experiments per hour—take up to a year, or more, of continuous effort, to empirically identify optimal conditions.

To improve the throughput of the cuvette-based approach, multi-well electroporation systems were developed, but existing devices carry several disadvantages. The 96-well Shuttle™ system made by Lonza, for example, offers medium-throughput transformation but is applicable only for mammalian cells and still requires extensive manual pipetting. Another example is the 96-well electroporation plate made by BTX; however, BTX's plates suffer from a high rate of arcing events and malfunction once encountering the arcing issue. On this basis, there is a pressing need to develop a scalable, high-throughput electroporation platform that is compatible with commercially available liquid handling robots for automated pipetting and addresses the shortcomings of existing systems.

High-throughput flow electroporation devices are provided that include independent channels which can be scaled to any size (e.g., 96 channel, 128 channel, etc.). The device, in its assembled state, can thereby allow for several independent electroporation experiments to be performed simultaneously.

In an example configuration, an assembled device includes at least five layers: holder-electrode-channel-electrode-holder, as shown in FIG. 4. The holder layers (alternatively referred to as support layers or support layer components) can provide electrical isolation as a safety precaution during operation of the device as well as provide for structure that can assist with self-sealing and handling of the assembly. The electrode layers (alternatively referred to as conductive layers), when connected to a power supply, can provide an electric field in each of the flow channels, (e.g., 96 channels, as shown in FIG. 4). The channel layer(s) define the flow channels in which electroporation occurs. Because of the layered configuration, the high-throughput flow electroporation device can be readily fabricated using standard techniques (e.g., CNC machining and laser cutting). In addition, nozzle-like components can be added at the fluid exits (e.g., at the bottom of the bottom holder) to isolate each electroporated sample from one other and guide the sample fluid into corresponding collection wells or tubes.

An electroporation assembly can include any of the optional features that follow, in any combination. The terms "layer" and "layer component" are used interchangeably and refer to discrete component parts of an electroporation assembly.

Top or Inlet-Side Support Layer Component: a) can comprise an electrically insulating material; b) can be removeable, reusable, interchangeable, and/or autoclavable; c) can fully or partially cover an electrode layer; d) can be configured to receive fluid from a cell suspension source, e.g., pipette tips filled with cell suspension; e) can accept or include o-rings or an insulating rubber layer to prevent fluid leakage; and/or f) can be connectable/bondable to the cell suspension source so as not to expose a flow of cell suspension to air, which can be helpful for application of the device to electroporation of aerobic cells.

Bottom or Outlet-Side Support Layer Component: a) can comprise an electrically insulating material; b) can be removeable, reusable, interchangeable, and/or autoclavable; c) can fully or partially covers an electrode layer; d) can be connectable/bondable to a cell collection unit so as not to expose a flow of cell suspension to air, which can be helpful for application of the device to electroporation of aerobic cells; and/or e) can include or be configured to receive nozzles.

Conductive or Electrode Layer Component(s): a) can include a top electrode layer and a bottom electrode layer, or two electrode layers arranged in an alternate configuration (e.g., side-by-side configuration with a channel layer disposed between); b) can comprise electrically conductive materials; c) can be removeable, reusable, interchangeable, and/or autoclavable; d) can be configured to control the electrical field within each of the plurality of electroporation flow paths; e) can be configurable to produce an electric field within all of the plurality of electroporation flow paths at once, or to independently produce an electric field within one or more of the plurality of electroporation flow paths at a time; f) can include a plurality of self-sealing structures disposed at each of the electroporation flow paths (e.g., on the bottom surface of the top electrode layer and on the top surface of the bottom electrode layer); g) the self-sealing structures can be configured to serve as a self-sealing and self-bonding mechanism when assembled with counterpart structures of the channel layer; h) the self-sealing structures can be a portion of the electrode layer or embedded in the electrode layer; i) the self-sealing structures can be made of the same material as the electrode layer or made of other electrically conductive material; j) can include a plurality of nozzles disposed at the electroporation flow paths (e.g., on the bottom surface of the bottom electrode layer); and/or k) the nozzles can be configured to direct a flow of a cell suspension travelling through the electroporation flow paths into the cell collection unit.

Channel Layer Component(s): a) can comprise an electrically insulating material; b) can be removeable, disposable, reusable, interchangeable, and/or autoclavable; c) can be configurable to have a cross-section of each channel be of different sizes and shapes including, but not limited to, a basic straight shape, converging shape, diverging shape, bilateral shape, etc.; d) can include a plurality of self-sealing structures disposed at the electroporation flow paths (e.g., on the top surface, the bottom surface, or at both the top surface and the bottom surface of the channel layer); e) the self-sealing structures can be configured to serve as a self-sealing and self-bonding mechanism when assembled with the counterparts on the electrode layers; f) the self-sealing structures can be a portion of the channel layer or embedded in the channel layer; and/or g) the self-sealing structures can be made of the same material as the electrode layer or made of other electrically insulating materials.

The uniqueness and advantages of the provided high-throughput electroporation devices lie in several aspects, as follows.

(1) Simple fabrication: The layered-configuration of the device allows one to fabricate the device readily by standard, widely available manufacturing techniques such as CNC machining, injection molding, laser cutting, etc. The layered configuration can further provide for a reusable electroporation device. For example, the channel layer(s) may be replaced after each experiment as a disposable part, while the conductive layers and support layers are retained and reused. A reusable electroporation device can be commercially and academically valuable.

(2) Flow-through based electroporation: The proposed device performs electroporation by continuously flowing bacteria samples through flow channels (e.g., microfluidic flow channels) with electrical fields established in the channels. Compared to commercial products such as the 96-well electroporation plates from BTX, which perform electroporation in a stop flow (similar to cuvette-based electroporation), the provided device performs electroporation in a continuous, flow-through manner. Such flow-through manner may not only lead to improved cell viability and transformation efficiency, but also reduce the rate of arcing events.

(3) Highly compatible with commercially available liquid handling robots: Because of its fabrication and operation, the proposed electroporation device is compatible not only with manual pipetting processes but also with commercially available automated pipetting systems (e.g., liquid handling robots). FIG. 4 schematically illustrates integration of a high-throughput electroporation device with a liquid handling robot with 96 tips and a 96-well plate. Such integration can allow 96 independent electroporation experiments to be performed simultaneously in a single operation. Given that both liquid handling robots and 96-well plates have long been commercialized and widely used, the high-throughput electroporation device can readily integrate with existing devices to enable automated, high-throughput bacteria transformation.

(4) Versatile electroporation operation: Owing to the layered-configuration, the electrodes of the proposed device can be fabricated in a manner such that the 96 samples can be, respectively, subject to 96 different electrical conditions, thereby enabling the rapid screening of electrical conditions that can lead to successful genetic transformation. Alternatively, the electrodes can be fabricated such that a single electrical condition can be applied to the 96 samples in parallel and simultaneously with use of a robot arm with 96-tip head. With such a configuration, up to 12 different electrical conditions can be also applied to the 96 samples when using a robot arm with 8-tip head.

By leveraging automated liquid handling, this technology facilitates high throughput, parallel, automated transfection of both prokaryotic and eukaryotic cells. The technology disclosed here can be of use to the research and development of any novel genetically engineered cell for a variety of applications in synthetic biology, industrial biotechnology, drug discovery, and the human microbiome.

EXEMPLIFICATION

Example 1

Prototype Device with 16 Channels

Figure 5A:
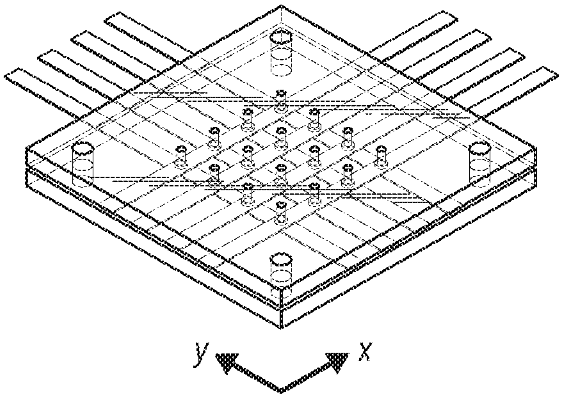
FIG. 5A is a photograph of an assembled proof-of-concept electroporation assembly.

Using Computer Numerical Control (CNC) machining, the five layers illustrated in FIG. 4 were fabricated and assembled into a proof-of-concept electroporation device, as shown in FIG. 5A. The proof-of-concept device was fabricated to have 16 electroporation channels for preliminary experiments. The two holder layers and the channel layer were made of acrylic, while the two electrode layers, which were connected to a power supply, were made of aluminum. Between each layer, chemical-resistant, electrically-insulating tapes were used to firmly assemble these five layers together and also to serve as sealing gaskets to prevent fluid leakage during fluid flow through each of the channels. Once the five layers were assembled together, pipette tips of ~15 mm long that were cut out of standard 1000-μL pipettes tips were used as nozzle-like components and embedded into the holes at the bottom of the bottom holder, as depicted in FIG. 4, to complete the fabrication of the proof-of-concept device.

Figure 5B:
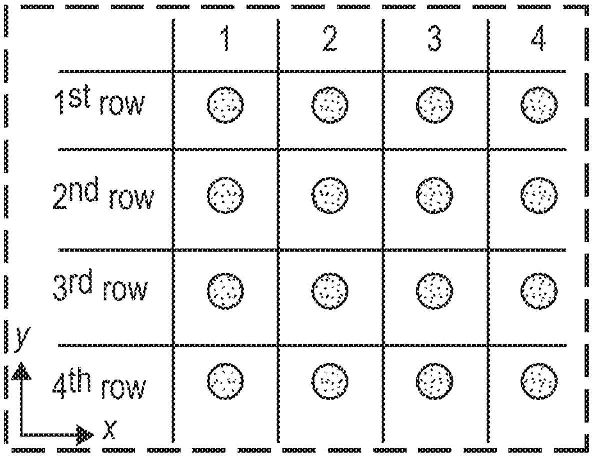
FIG. 5B is a schematic illustrating the configuration of the electroporation assembly of FIG. 5A, including a layout for conducting four electroporation experiments in parallel on a row-by-row basis.

To test if the proof-of-concept device would work as proposed and examine the uniformity of transformation efficiency over the 16 channels, electroporation on *E. coli* DH10β was performed by running 4 electroporation experiments in parallel on a row-by-row basis (FIG. 5B). In these preliminary experiments, the *E. coli* suspension samples were manually aspirated and dispensed using a multichannel pipette with only 4 pipette tips on. This preliminary electroporation experiment can be briefly described by three steps. First, the multichannel pipette aspirated a given volume of samples and then brought the 4 pipette tips down into the channels in the first row on the top holder layer. Second, the samples were immediately dispensed into the proof-of-concept device after the electrodes were driven by the power supply at a voltage of 2.5 kV with a pulse of 5 ms. Upon the application of the electrical pulse, the *E. coli* samples were exposed to an electrical field when flowing through the flow channels in the middle channel layer. Last, the electroporated *E. coli* samples were guided by the nozzles and then collected into four separate 1.5 mL microcentrifuge tubes. By repeating these three steps, all 16 electroporation experiments were completed within 2 minutes at a rate of 20~30 seconds per row. The use of liquid handling robots rather than manual multichannel pipetting, as performed here, was estimated to be able to provide for a reduction in processing time of at least 50%, or to within 1 minute.

Figure 5C:
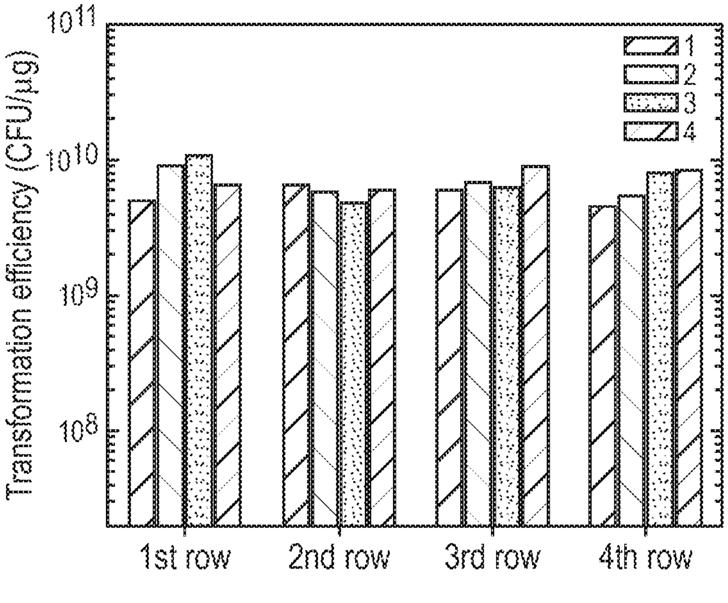
FIG. 5C is a plot illustrating transformation efficiency for *E. coli* DH10β obtained from different channels in the proof-of-concept device of FIG. 5A. Each channel, regardless of its location, yielded a transformation efficiency within the range of 4.72×109~$1.11\times10^{10}$ CFU/μg, which is comparable to that obtained using standard cuvettes. The transformation efficiency can be considered uniform over the 16 channels, either within the same row or across different rows.

Regarding transformation efficiency, each of the 16 channels appeared to yield a distinct transformation efficiency ($4.72\times10^{9}$~$1.11\times10^{10}$ CFU/μg) that is comparable to that obtained using cuvettes at the same voltage (FIG. 5C). The difference in the transformation efficiency among different channels within the same row and across the different rows can be considered insignificant, because the biggest difference is even less than an order of magnitude. Overall, the preliminary results verified that the proposed layered-configuration of a high throughput flow device can perform bacteria electroporation for genetic transformation. Moreover, the transformation efficiency obtained from each of the 16 channels, though slightly different from each other, can be considered uniform.

Example 2

Prototype Device with 96 Channels

Figure 6A:
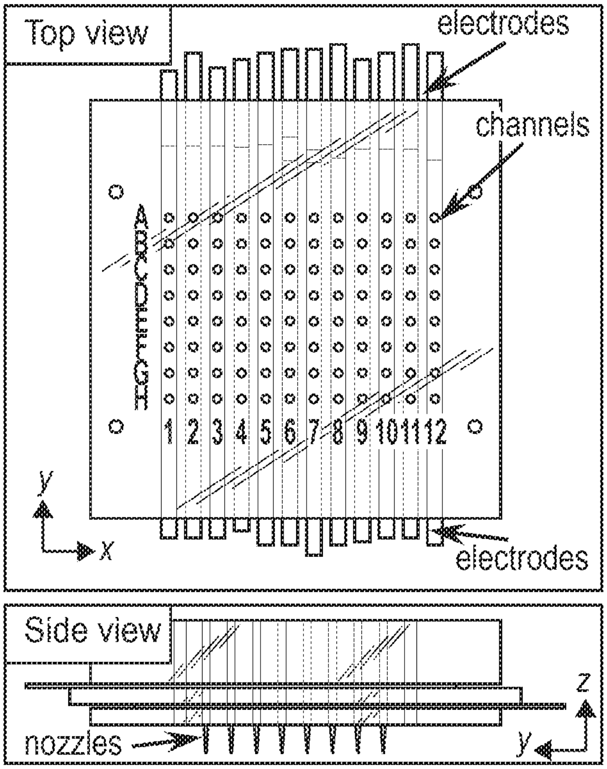
FIG. 6A is a photograph of another assembled proof-of-concept electroporation assembly for a 96-well configuration.
Figure 6B:
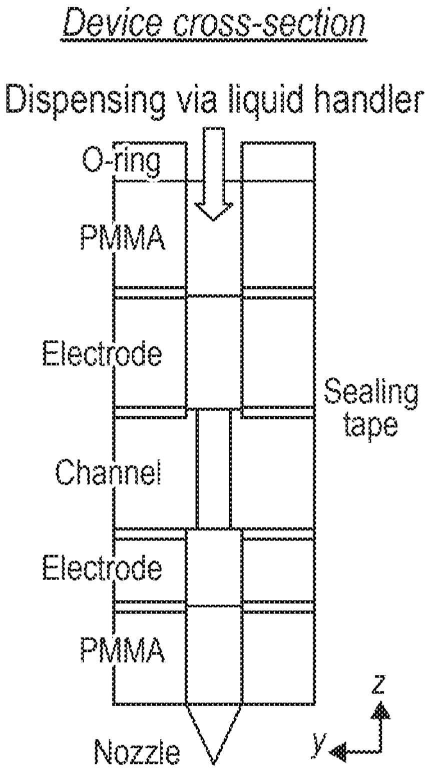
FIG. 6B is a schematic illustrating the layered structure of the assembly of FIG. 6A.
Figure 6C:
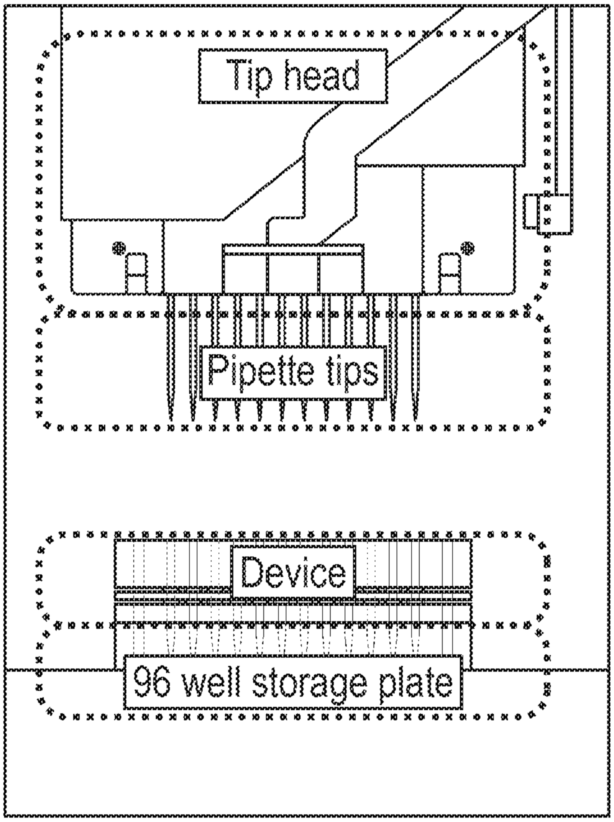
FIG. 6C is a photograph of an electroporation system to include the electroporation assembly of FIG. 6A.

To further prove the concept, an electroporation device with a 96-channel format was successfully prototyped (FIG. 6A). This 96-channel format is complementary to standard, commercially-available 96-well products in terms of its arrangement (8×12) and inter-well distance, making the scaled-up, proof-of-concept device compatible with those standard 96-well products. Briefly and similarly, the scaled-up device is prepared by assembling five layers, which were CNC machined, and between each layer, chemical-resistant, electrically-insulating tapes were used to firmly assemble these layers together and to serve as sealing gaskets to prevent fluid leakage (FIG. 6B). The 96-channel format, layered, compact device was integrated with a commercially-available liquid handling robot (PerkinElmer, Inc.) for transfer and dispensing of samples, and accommodated by a widely-used 96-well storage plate, for sample storage (FIG. 6C).

Figure 7A:
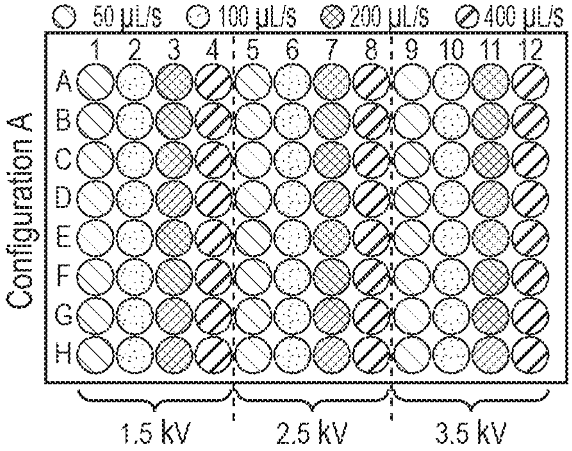
FIG. 7A is an illustration of a configuration of electroporation conditions of an experiment performed with a sample device. Three different voltages and four different dispensing flow rates were tested. Electroporation was conducted on a column-by-column basis (8 channels at a time), and, therefore, 12 different combinations of electroporation conditions were tested.
Figure 7B:
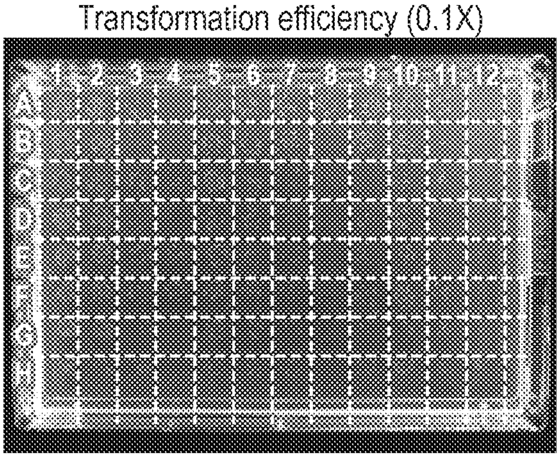
FIG. 7B is a photograph showing the colony forming units (CFUs) on a selection agar plate (with antibiotics), which demonstrated the capability of the device to perform electroporation in a 96-well format.
Figure 7C:
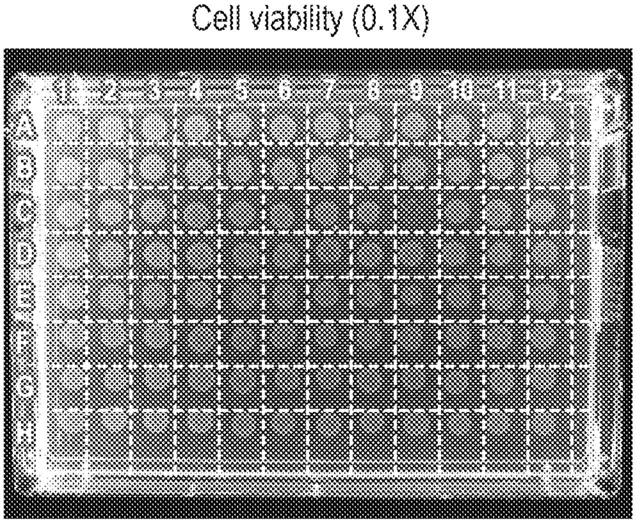
FIG. 7C is a photograph showing cell viability on a normal agar plate (without antibiotics), which demonstrated the device's ability to preserve cell viability after electroporation. Dilution ratio: 0.1×.

Upon successfully integrating the scaled-up device with the liquid handling robot, electroporation experiments in a high-throughput, semi-automated fashion were performed. The electroporation experiments were conducted in 8 channels at a time on a column-by-column basis, and 12 different combinations of electroporation conditions were tested on a high-transformation-efficiency strain of *E. coli* DH10β (FIG. 7A). The electroporation experiments were performed in all 96 channels on a column-by-column basis in 25~30 mins at a rate of ~2 min per column. The assembly successfully electro-transformed cells in most of the 96 wells on a selection agar plate (FIG. 7B), except for certain wells where extreme electroporation conditions were applied (e.g., a flow rate of 400 μL/sec). Moreover, the device performed electroporation without killing or damaging every cell in each channel, as cells remained viable and grew overnight on a control agar plate (FIG. 7C).

Figure 7D:
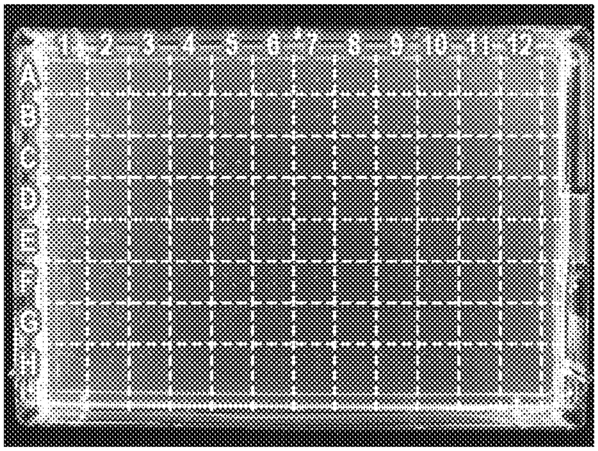
FIG. 7D is a photograph showing CFUs at a dilution ratio of 0.01× on a selection agar plate.
Figure 7E:
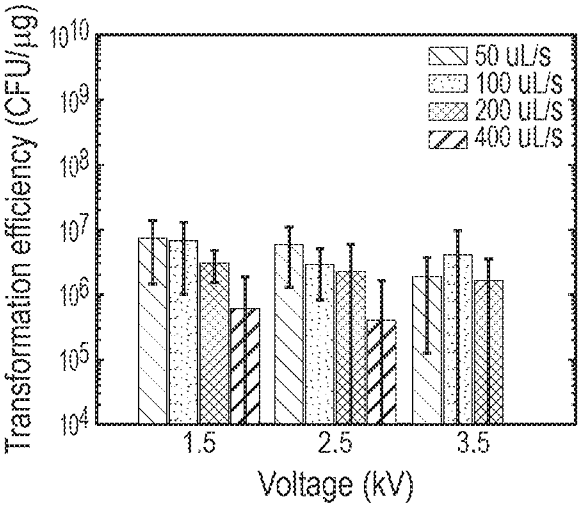
FIG. 7E is a graph of calculated transformation efficiencies corresponding to different applied voltages.
Figure 7F:
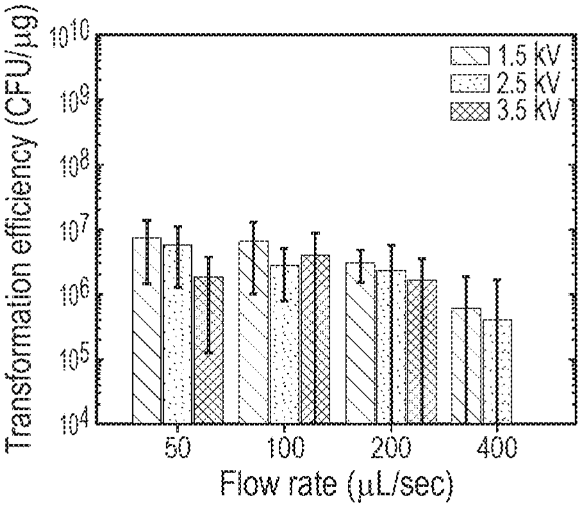
FIG. 7F is a graph of calculated transformation efficiencies corresponding to different flow rates. The graphs of FIGS. 7E and 7G reveal that the transformation efficiency degraded as the flow rate and voltage were increased.

With the device, which combination of electroporation conditions that can lead to viable and efficient transformation were easily ascertained by counting and comparing the number of CFUs on the selection plate with a dilution ratio of 0.01× (FIG. 7D). For example, the results suggest that, irrespective of applied voltages, lowering the flow rate for sample dispensing can dramatically improve the transformation efficiency (FIG. 7E), while reducing the applied voltage (e.g., weakening the field strength) in this setting can moderately improve efficiency (FIG. 7F).

Figure 7G:
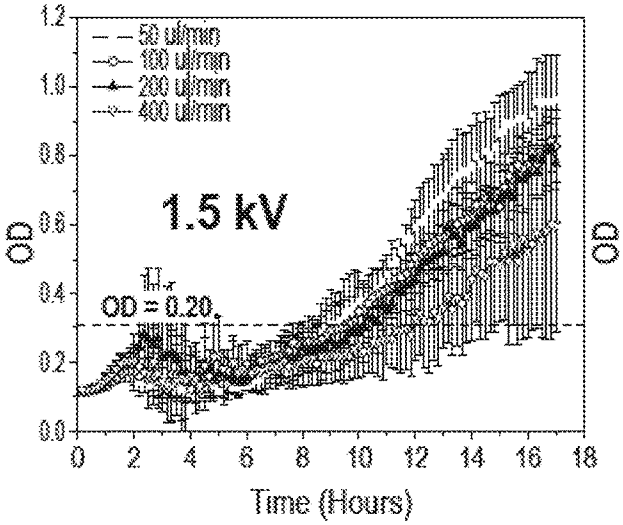
FIG. 7G is a plot illustrating the overnight growth curves of bacteria samples electroporated under 1.5 kV conditions and monitored.
Figure 7H:
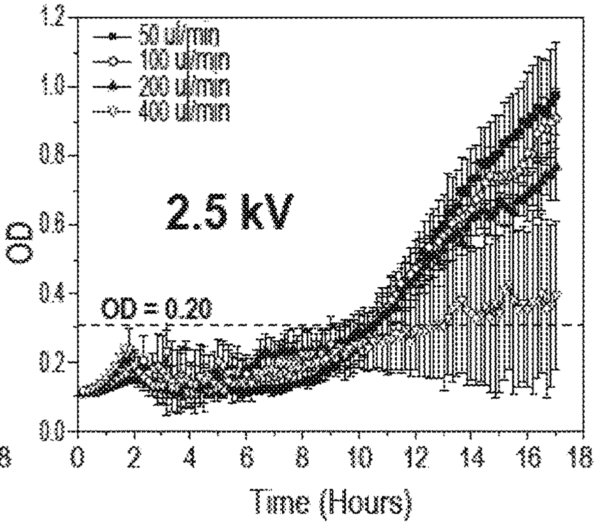
FIG. 7H is a plot illustrating the overnight growth curves of bacteria samples electroporated under 2.5 kV conditions and monitored.
Figure 7I:
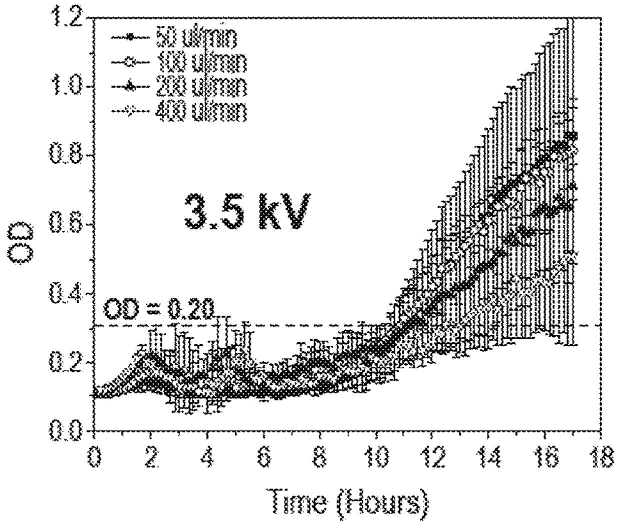
FIG. 7I is a plot illustrating the overnight growth curves of bacteria samples electroporated under 3.5 kV conditions and monitored. The growth curves of FIGS. 7G-7I indicate that, as the flow rate and voltage increased, bacteria grew slower (i.e., took a longer time to grow to a certain Optical Density (OD) value, in particular, an $OD_{600}$ value (optical density measured at a wavelength of 600 nm), where lower OD values indicate lower bacterial cell concentrations, and higher OD values indicate higher bacterial cell concentrations). In other words, the initial number of bacterial cells that were successfully transformed were less in the samples that were electroporated under higher flow rates and voltages. A growth curve can thus be an alternative measure to evaluate the transformation efficiency without counting CFUs.

Overall, regardless of the flow rate and applied voltage, transformation efficiencies ranging from $10^{5}$ to $10^{7}$ CFU/μg-DNA were achieved with the device at this specific setting. Manually and visually counting CFUs in 96-well format can also be time-consuming and undesirable. On this basis, the possibility of using growth curves of cells as an alternative to CFU counting was explored in order to characterize transformation efficiencies. As shown in FIGS. 7G-7I, overnight growth curves reveal that, as the flow rate is decreased, cells grow faster with a deeper slope, which implies that the initial number of cells that are successfully electroporated are higher in the settings of lower flow rates. Taken altogether, these results demonstrate that the device can interface with commercially-available liquid handling robots and standard size (e.g., 96-well) related products, and perform electroporation experiments in a multi-channel format with high transformation efficiency and cell viability. The device can serve as a tool to narrow down or identify proper range of electroporation conditions in order to achieve desired transformation efficiencies.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. An electroporation assembly for interfacing with a liquid handling system, comprising:

at least two electrically conductive layer components; and a channel layer component configured to be removably disposed between the at least two electrically conductive layer components, the at least two electrically conductive layer components and the channel layer component defining a plurality of parallel electroporation flow paths in an assembled state, wherein each component of the at least two electrically conductive layer components and the channel layer component defines a plurality of channels therethrough.

2. The electroporation assembly of claim 1, further comprising at least one support layer component configured to interface with one of the at least two electrically conductive layer components, the at least one support layer component comprising an electrically insulating material.

3. The electroporation assembly of claim 2, wherein the at least one support layer component is configured to seal against the one of the at least two conductive layer components.

4. The electroporation assembly of claim 2, wherein the at least one support layer component is an inlet support layer component defining a plurality of input ports configured to receive cell sample fluid from a manual pipette, an automated liquid dispenser, or an automated liquid handling system.

5. The electroporation device of claim 2, wherein the at least one support layer component is an inlet support layer component defining a plurality of input ports configured to connect with one or more cell sample reservoirs such that cell sample fluid entering the assembly from the one or more cell sample reservoirs is sealed.

6. The electroporation assembly of claim 2, wherein the at least one support layer component is an outlet support layer component defining a plurality of outlet ports.

7. The electroporation assembly of claim 6, wherein the outlet support layer component is configured to connect with one or more collection reservoirs such that cell sample fluid exiting the assembly to the one or more collection reservoirs is sealed.

8. The electroporation assembly of claim 6, wherein each of the plurality of outlet ports comprises a nozzle.

9. The electroporation assembly of claim 6, wherein one of the at least two conductive layer components comprises nozzles disposed at terminating ends of the electroporation flow paths, and wherein the plurality of outlet ports is configured to receive the nozzles.

10. The electroporation assembly of claim 1, wherein the at least two conductive layer components are removeable, reusable, interchangeable, autoclavable, or a combination thereof.

11. The electroporation assembly of claim 1, wherein at least one of the at least two conductive layer components is uniformly conductive.

12. The electroporation assembly of claim 1, wherein at least one of the at least two electrically conductive layer components comprises selectively activatable electrodes capable of producing electric fields that vary in at least one of strength and timing for a subset of the plurality of electroporation flow paths.

13. The electroporation assembly of claim 1, wherein one of the at least two conductive layer components comprises nozzles disposed at a terminating end of each of the plurality of parallel electroporation flow paths, the nozzles configured to direct a flow of a cell sample fluid travelling through each of the electroporation flow paths into corresponding receptacles of a cell collection unit.

14. The electroporation assembly of claim 1, wherein the channel layer component comprises an electrically insulating material.

15. The electroporation assembly of claim 1, wherein the channel layer component is removeable, reusable, interchangeable, autoclavable, or a combination thereof.

16. The electroporation assembly of claim 1, wherein the channel layer component defines a constriction region of each of the plurality of electroporation flow paths, a geometry of at least a subset of the construction regions comprising a uniform cross-sectional area.

17. The electroporation assembly of claim 1, wherein the channel layer component defines a constriction region of each of the plurality of electroporation flow paths, a geometry of at least a subset of the construction regions comprising a varying cross-sectional area providing for a converging channel, a diverging channel, or a converging and diverging channel.

18. The electroporation assembly of claim 1, further comprising at least one additional channel layer component, each of the channel layer component and the at least one additional channel layer component defining a portion of the plurality of electroporation flow paths.

19. The electroporation assembly of claim 1, wherein at least one of the conductive layer components comprises a sealing structure configured to engage with a complimentary sealing structure of the channel layer component.

* * * * *